(12) United States Patent
Wostbrock et al.

(10) Patent No.: US 7,907,283 B2
(45) Date of Patent: Mar. 15, 2011

(54) METHOD AND DEVICE FOR DETERMINING THE TOTAL OXYGEN CONTENT AND/OR THE TOTAL CARBON CONTENT IN AMMONIA

(75) Inventors: Karl-Heinz Wostbrock, Mannheim (DE); Walther Schmid, Mannheim (DE)

(73) Assignee: BASF SE, Ludwigshafen (DE)

( * ) Notice: Subject to any disclaimer, the term of this patent is extended or adjusted under 35 U.S.C. 154(b) by 366 days.

(21) Appl. No.: 12/282,996

(22) PCT Filed: Mar. 22, 2007

(86) PCT No.: PCT/EP2007/052752
§ 371 (c)(1),
(2), (4) Date: Sep. 15, 2008

(87) PCT Pub. No.: WO2007/110365
PCT Pub. Date: Oct. 4, 2007

(65) Prior Publication Data
US 2009/0066958 A1    Mar. 12, 2009

(30) Foreign Application Priority Data
Mar. 28, 2006   (DE) .......................... 10 2006 014 278

(51) Int. Cl.
*G01N 31/12* (2006.01)
*G01N 21/35* (2006.01)
(52) U.S. Cl. ..................... 356/437; 356/237.1; 356/300; 203/3; 203/50; 423/237
(58) Field of Classification Search ............... 356/237.1, 356/437, 300; 203/1, 3, 6, 57, 67, 68, 71; 423/235–239.1
See application file for complete search history.

(56) References Cited

U.S. PATENT DOCUMENTS
4,077,780 A * 3/1978 Doshi ............................. 95/100
(Continued)

FOREIGN PATENT DOCUMENTS
JP            08201370         8/1996

OTHER PUBLICATIONS
Olin, J. B. et al., "Thermal Decomposition and Partial Oxidation of Ammonia", Journal of Chemical and Engineering Data, vol. 6, No. 3, pp. 384-389, XP-002443460, (1961).

(Continued)

*Primary Examiner* — Gregory J Toatley
*Assistant Examiner* — Rebecca C Slomski
(74) *Attorney, Agent, or Firm* — Oblon, Spivak, McClelland, Maier & Neustadt, L.L.P.

(57) ABSTRACT

The invention relates to a process for determining the total oxygen content and the total carbon content in ammonia, in which ammonia is first split into nitrogen and hydrogen, then the oxygen still present in the ammonia is reacted essentially fully with hydrogen to give water and the carbon still present is reacted essentially fully with hydrogen to give methane. In a next step, the water content and the methane content in the gas are determined. Finally, the total oxygen content is determined from the water content and the total carbon content from the methane content. The invention further relates to an apparatus for performing the process, which comprises a cracker for splitting the ammonia and for converting the oxygen- and/or carbon-comprising compounds, and at least one cavity ring-down spectrometer for detecting the water content and/or carbon content. The cracker and the at least one spectrometer, and also all devices and connecting lines between the cracker and the spectrometer, are surrounded by an inert gas.

15 Claims, 2 Drawing Sheets

U.S. PATENT DOCUMENTS

2003/0080295 A1   5/2003   Webber et al.
2005/0122523 A1   6/2005   Yan

OTHER PUBLICATIONS

Choudhary, T.V. et al., "CO-free fuel processing for fuel cell applications", Catalysis Today, Elsevier, vol. 77, No. 1-2, pp. 65-78, XP-002443461, (2002).

Collins, John P. et al., "Catalytic decomposition of ammonia in a membrane reactor", Journal of Membrane Science, Elsevier, vol. 96, No. 3, pp. 259-274, XP004041525, (1994).

* cited by examiner

METHOD AND DEVICE FOR DETERMINING THE TOTAL OXYGEN CONTENT AND/OR THE TOTAL CARBON CONTENT IN AMMONIA

The invention relates to a process and to an apparatus for determining the total oxygen content and the total carbon content of ammonia which is intended to be designated as high-purity and, if appropriate, comprises oxygen- and/or carbon-comprising compounds. The process and the apparatus are suitable in particular for the determination of the total oxygen content and/or of the total carbon content in high-purity ammonia.

High-purity ammonia is gaining ever greater industrial significance in the light-emitting diode (LED) production sector. Such light-emitting diodes comprise a light-emitting body which is generally produced by an epitaxy process. This means that the light-emitting body is produced by a layer-by-layer buildup of atoms. High-performance light-emitting diodes, i.e. light-emitting diodes with a high light output, are generally manufactured from GaN on SiC. The nitrogen required for this purpose is supplied from ammonia in the production process. Since every extraneous atom, especially oxygen and carbon atom, weakens the light output of the LED, it is necessary to use high-purity ammonia. This need for high-purity ammonia makes it necessary to detect oxygen and carbon even in the slightest traces.

JP-A 08-201370 discloses a process for measuring moisture present in traces in ammonia. To this end, the ammonia is split into nitrogen and hydrogen in a catalyst-comprising vessel at a temperature in the range from 600 to 1000° C. The moisture content is subsequently determined by a moisture-measuring device, preferably a dew point instrument or an infrared spectrophotometer. The process carried out in this way allows moisture contents in the ammonia of from 1 to 10 ppm to be determined. However, this measurement accuracy is insufficient to satisfy the specifications which are placed on high-purity ammonia.

A measurement process with which the water content in a gas stream can be determined down to a detection limit of 0.2 ppb and the methane content in a gas stream down to a detection limit of 2 ppb is cavity ring-down spectroscopy. This is known, for example, from US-A 2005/0122523. Corresponding equipment is sold, for example, by TigerOptics. However, it is evident from the specification for these instruments that they are not suitable for determining water or methane in ammonia. The cause of this is the similar spectra of water, methane and ammonia.

A further disadvantage of the processes known from the prior art is that it is possible in each case to determine only the water content or the methane content. However, ammonia produced on the industrial scale comprises not only water and methane but also further oxygen- and/or carbon-comprising compounds. These compounds are, for example, longer-chain hydrocarbons, carbon monoxide, carbon dioxide and molecular oxygen. These compounds too comprise oxygen or carbon, which can be introduced into a diode layer as an extraneous atom, for example in the course of production of LEDs.

It is therefore an object of the present invention to provide a process by which the total oxygen content and the total carbon content can be determined even in slight traces in ammonia which is intended for designation as high-purity and, if appropriate, comprises oxygen- and/or carbon-comprising compounds.

It is a further object of the invention to provide an apparatus for performing the process.

The object is achieved by a process for determining the total oxygen content and the total carbon content of ammonia which is intended to be designated as high-purity and, if appropriate, comprises oxygen- and/or carbon-comprising compounds, comprising the following steps:
a) splitting the ammonia into nitrogen and hydrogen;
b) essentially fully reacting the oxygen of all oxygen-comprising compounds with hydrogen to give water and the carbon of all carbon-comprising compounds with hydrogen to give methane;
c) determining the water content and the methane content in the gas;
d) determining the total oxygen content from the water content and the total carbon content from the methane content.

The ammonia in which the total oxygen content and/or the total carbon content are determined may be present either in liquid or gaseous form. The process is suitable for determining the total oxygen content and/or the total carbon content both in liquid and gaseous ammonia. To determine the total oxygen content and/or the total carbon content, a sample is taken and is split into hydrogen and nitrogen. The sample may be taken either as an individual random sample or else preferably continuously. Owing to the high temperature which is required to split the ammonia into hydrogen and nitrogen, the ammonia which is supplied to the measurement is already entirely in gaseous form before the splitting in the determination of the total carbon content and/or of the total oxygen content in liquid ammonia.

As a result of the splitting of all oxygen-comprising compounds and all carbon-comprising compounds and their recombination to water and to methane, it is possible in accordance with the invention to determine the total oxygen content and the total carbon content in a simple manner only by determining the water content and the methane content.

A further advantage in the process according to the invention of determining all oxygen- and carbon-containing compounds by converting them to water and methane respectively is that especially $CO_2$ enters into a large number of compounds with ammonia and for this reason is difficult to isolate and to detect quantitatively. Since it is generally sufficient when the proportion of extraneous atoms in the ammonia is known, irrespective of the compound in which they are present, it is sufficient to determine the total carbon content and the total oxygen content and not the presence of individual compounds which contaminate the ammonia. A further advantage of the process according to the invention by virtue of the detection of the total oxygen content and of the total carbon content is that it is not the case that an individual detection limit is crucial for each substance and these detection limits thus add up for the total impurities, but rather that, as a result of the conversion to water or methane, one detection limit for oxygen and one detection limit for carbon is sufficient in each case and therefore the total carbon content or total oxygen content can be detected down to a detection limit which is lower than the sum of the individual detection limits in the case of separate detection of the impurities.

As a result of the virtually full splitting of ammonia into nitrogen and hydrogen, the ammonia content after the splitting is less than 1 ppm, and, owing to the compounds which comprise carbon or oxygen and are present only in traces, and owing to the high hydrogen excess, the oxygen present in molecular form or in compounds in the gas stream is converted essentially fully to water and the carbon present in compounds in the gas stream is converted essentially fully to methane. "Essentially fully converted" in the context of the present invention means that at least 98% by volume, preferably at least 99% by volume and in particular at least 99.5% by volume of the oxygen and carbon present is converted to water and methane respectively.

In a preferred embodiment, the splitting of the ammonia into nitrogen and hydrogen and the conversion of the oxygen- and/or carbon-comprising compounds present in the ammonia with hydrogen to give water and/or methane are carried out in the presence of a catalyst. The splitting of the ammonia and the conversion of the oxygen- or carbon-comprising compounds present in the ammonia to water and methane can be carried out in any reactor known to those skilled in the art. Suitable reactors are, for example, tubular reactors, moving bed reactors or fluidized bed reactors. However, the performance of the process is independent of the type of reactor. Since the main task of the reactor is the splitting of the ammonia into nitrogen and hydrogen, the reactor is also referred to as the cracker.

The catalyst may, for example, be present as a coating of the reactor wall. In the case of moving bed or fluidized bed reactors, the fluidized bed or moving bed granule preferably comprises the catalyst. In a further embodiment, it is also possible, for example, to introduce catalyst-comprising random packings or other catalyst-comprising internals into a tubular reactor. The catalyst may be applied to the random packings or internals, for example, as a coating. However, it is also possible to manufacture the random packings or internals entirely from catalyst material. A further possibility is to use a material which comprises the catalyst on a support material for the fluidized bed or moving bed granule, the random packings or the internals.

Suitable catalysts for splitting the ammonia into nitrogen and hydrogen and for converting the oxygen of the oxygen-comprising compounds to water and the carbon of the carbon-comprising compounds to methane are, for example, noble metals. Preferred catalysts are silver and all catalysts which are known to those skilled in the art and with whose aid ammonia can be synthesized.

In a preferred embodiment, the water content and/or the methane content are determined by cavity ring-down spectroscopy. The splitting of the ammonia into hydrogen and nitrogen eliminates the interference by the ammonia in the spectroscopic measurement. Since the splitting of 1 mole of ammonia forms 2 moles of hydrogen and nitrogen, this results in doubling of the volume of the gas stream. In order to determine the content of oxygen or carbon atoms in the ammonia, the value determined therefore likewise has to be doubled. For example, at a measured water content of 5 ppb in the gas stream, 10 ppb of water are actually present in the ammonia.

In a preferred embodiment, the splitting of the ammonia and the conversion of the oxygen- and/or carbon-comprising compounds to water and methane respectively is effected at a temperature of at least 600° C., preferably of at least 800° C., more preferably of at least 900° C. At this temperature, the oxygen from all oxygen-comprising compounds is converted essentially fully to water and the carbon from all carbon-comprising compounds is converted essentially fully in the presence of the above-described catalyst.

In general, the splitting of ammonia to hydrogen and nitrogen and the reaction of the oxygen of all oxygen-comprising compounds and/or of the carbon of all carbon-comprising compounds to give water and methane proceed essentially simultaneously. These reactions are generally carried out in a cracker whose walls are coated on the inside with silver. In order to achieve a larger catalyst surface area, the cracker may also be filled with catalyst-comprising granule which is flowed through by the ammonia to be split. However, it is also possible first to split the ammonia into nitrogen and hydrogen in one reactor and then to convert the oxygen of the oxygen-comprising compounds and the carbon of the carbon-comprising compounds to water and methane respectively in a second reactor. This is advisable especially when different catalysts and/or different temperatures are used to split the ammonia and to convert the oxygen and the carbon. In this case, one reactor comprises a catalyst suitable for splitting the ammonia and is operated at a temperature suitable for splitting the ammonia, while the second reactor comprises a catalyst which is suitable for reacting the oxygen of the oxygen-comprising compounds with hydrogen to give water and the carbon of the carbon-comprising compounds with hydrogen to give methane, and is operated at a temperature suitable for this purpose.

In the case of use of cavity ring-down spectroscopy to detect the water content or the methane content in the gas, different instruments in each case, or else multichannel instruments in which an individual measurement can be carried out in each channel, are required. Thus, one instrument for determining the water content and one instrument for determining the methane content are used. With cavity ring-down spectroscopy, the detection limit is 0.2 ppb for water in the gas and 2 ppb for methane, which means in each case ppb by volume.

The instruments with which the water content and the methane content are determined in the gas are connected in series in one embodiment. In this case, the gas preferably flows first through the spectrometer in which the water content is determined and then the spectrometer in which the methane content is determined. Subsequently, the gas is released to the environment as offgas. It will be appreciated that it is also possible to measure the methane content in the first spectrometer and the water content in the second spectrometer.

In a further embodiment, the instruments for determining the water content and the methane content are connected in parallel. To this end, the gas stream is first divided. One substream is then fed to the instrument for measuring the water content and one substream to the instrument for measuring the methane content. On completion of the measurement, the gas is released to the environment here too, or conducted back into the production.

In order to prevent oxygen-comprising compounds or carbon-comprising compounds from the environment from getting into the gas stream in which the oxygen content or the carbon content is to be determined, the process is preferably conducted under an inert gas atmosphere. To this end, for example, there is inert gas flow around the cracker, if appropriate the further reactor, the measuring instruments and all connections between these devices. Suitable inert gases are all gases which comprise oxygen and carbon in small traces at most.

Preferred gases are noble gases, nitrogen, hydrogen and the gas mixture formed by the splitting of ammonia. The gas mixture formed by the splitting of ammonia is, for example, the offgas from the measuring process. A particularly preferred inert gas is nitrogen. The substances which interfere with the determination of the total carbon content and/or total oxygen content can alternatively also be avoided by conducting the process in an evacuated protective system.

In the case of conduct of the process in an evacuated protective system, the residual gas atmosphere consists preferably of the abovementioned inert gases.

Owing to the very small amounts of oxygen- and/or carbon-comprising compounds in the ammonia, for example, even the smallest leaks at connecting points, for example between a line and a measuring instrument or a line and the cracker, are sufficient to allow oxygen, water or carbon dioxide from the air to penetrate into the measuring system when there is no inert gas purge around it.

A further means of preventing oxygen- or carbon-comprising impurities from the environment from penetrating into the measuring system is to seal all connections, for example in a gas-tight manner. Typical gas-tight detachable connections are generally inadequate, since they cannot ensure that small traces do not diffuse through them. Owing to the large gas volume which the apparatus for measuring the total carbon content and/or the total oxygen content encloses, a technical-grade gas which still comprises up to 0.2% of extraneous gases is sufficient as inert gas, since the diffusion streams through the gas seals are generally so small that the impurities do not distort the measurement result.

It is not sufficient to operate the apparatus for determining the total oxygen content and the total carbon content under elevated pressure in order to prevent oxygen- or carbon-containing compounds from diffusing out of the environment into the gas to be analyzed. Even in the case of elevated-pressure operation, a portion of the gas always diffuses counter to the flow direction into the apparatus and thus distorts the measurement result.

According to the invention, the apparatus for performing the process for determining the total oxygen content and/or the total carbon content in ammonia comprises a cracker in which the ammonia is split into hydrogen and nitrogen and in which the oxygen- and/or carbon-comprising compounds are converted to water and methane, and at least one cavity ring-down spectrometer for detecting the water content and/or the carbon content. In this context, the cracker, the at least one spectrometer and all devices and connecting lines between the cracker and the spectrometer are surrounded by an inert gas. To this end, the cracker, the connections and the at least one spectrometer are accommodated in a container which is flooded with the inert gas.

Especially when different catalysts are used for ammonia splitting and for converting the oxygen and the carbon to water and methane, it is possible that a further reactor is connected downstream of the cracker. In this case, the ammonia is split in the cracker into hydrogen and nitrogen, and the oxygen of the oxygen-comprising compounds and the carbon of the carbon-comprising compounds are converted to water and methane in the reactor which follows.

However, it is also possible to conduct the process such that the splitting of the ammonia into hydrogen and nitrogen and the reaction of the oxygen of the oxygen-comprising compounds and of the carbon of the carbon-comprising compounds are effected together in a cracker. To this end, it is possible, for example, to coat the cracker with different catalysts so that the suitable catalyst required for each reaction is present.

The invention will be described in detail below with reference to a drawing.

In the drawing:

FIG. 1 shows a process flow diagram of a process according to the invention in which devices for measuring the water content and the methane content are connected in series.

Figure 1:
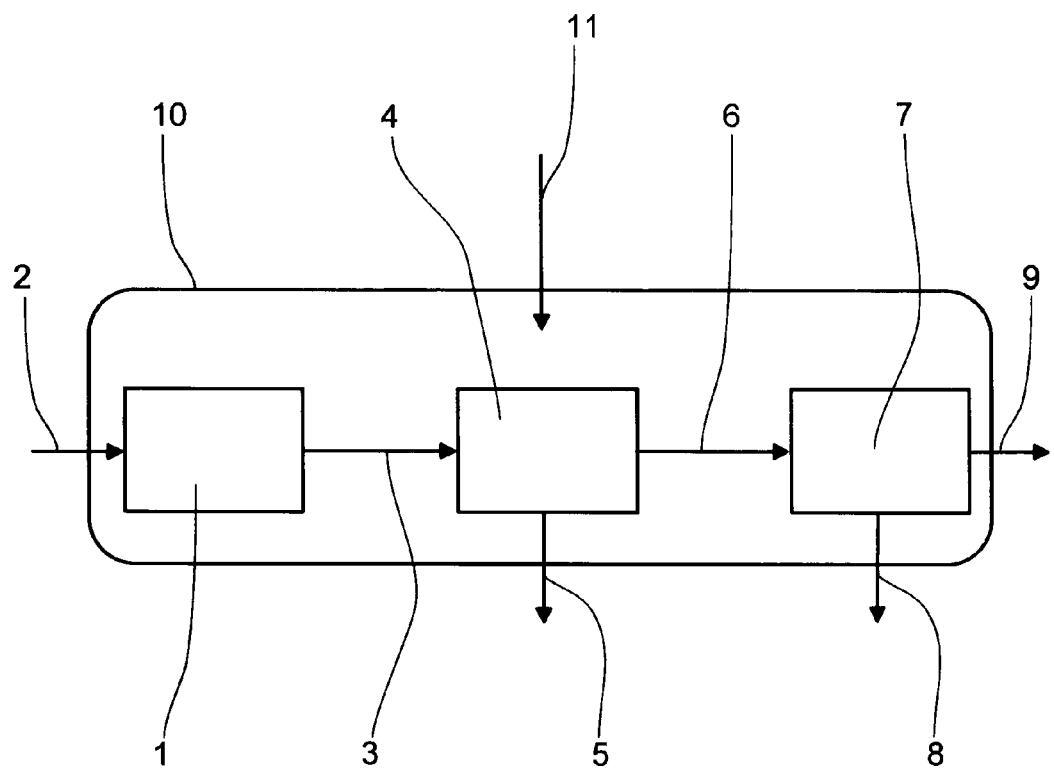
FIG. 1 shows a process flow diagram of the process according to the invention in which the water content and the methane content are determined in succession.

An ammonia stream 2 which still comprises traces of oxygen- and/or carbon-comprising compounds is fed to a cracker 1. In the cracker 1, the ammonia is split into nitrogen and hydrogen. At the same time, owing to the high hydrogen excess, the oxygen- and/or carbon-comprising compounds are converted to water and methane. For this purpose, the cracker 1 is preferably provided with a catalytically active coating. Suitable catalysts are, for example, silver and all catalysts with whose aid ammonia can be synthesized. Particular preference is given to silver. The cracker is preferably operated at a temperature of at least 600° C.

The gas stream 3 comprising hydrogen, nitrogen, water and methane, and also small amounts of ammonia which has not been split, is fed to a first cavity ring-down spectrometer 4. In the first cavity ring-down spectrometer 4, a small substream is branched off from the gas stream 3 comprising hydrogen, nitrogen, water, methane and small amounts of ammonia, and the water content is determined therein by cavity ring-down spectrometry. This substream is, as shown with the arrow with reference numeral 5, released to the environment after the measurement.

The remaining gas stream is, as shown with the arrow with reference numeral 6, fed to a second cavity ring-down spectrometer 7. In the second cavity ring-down spectrometer 7, a substream 8 is removed from the gas stream 6. The methane content is determined in the substream 8. Subsequently, the substream 8 is released to the environment. The remaining gas stream comprising hydrogen, nitrogen, water, methane and residues of ammonia is, as shown with the arrow with reference numeral 9, released to the environment. However, it is also possible to feed the gas stream to the ammonia synthesis again.

In order to prevent oxygen- and/or carbon-comprising compounds from being able to diffuse out of the environment into the cracker 1 or the cavity ring-down spectrometers 4, 7, the cracker 1 and the first cavity ring-down spectrometer 4 and the second cavity ring-down spectrometer 7 are enclosed by a casing 10. The casing 10 is flooded with an inert gas. Suitable inert gases are all gases in which the content of oxygen- and/or carbon-comprising compounds is preferably less than 0.2 ppb. Preferred inert gases are all noble gases or nitrogen; nitrogen is particularly preferred. In order to prevent inert gas from diffusing out of the casing 10 and being replaced by ambient air, it is possible to supply inert gas to the casing 10 via an inert gas feed, as shown with arrow 11.

Figure 2:
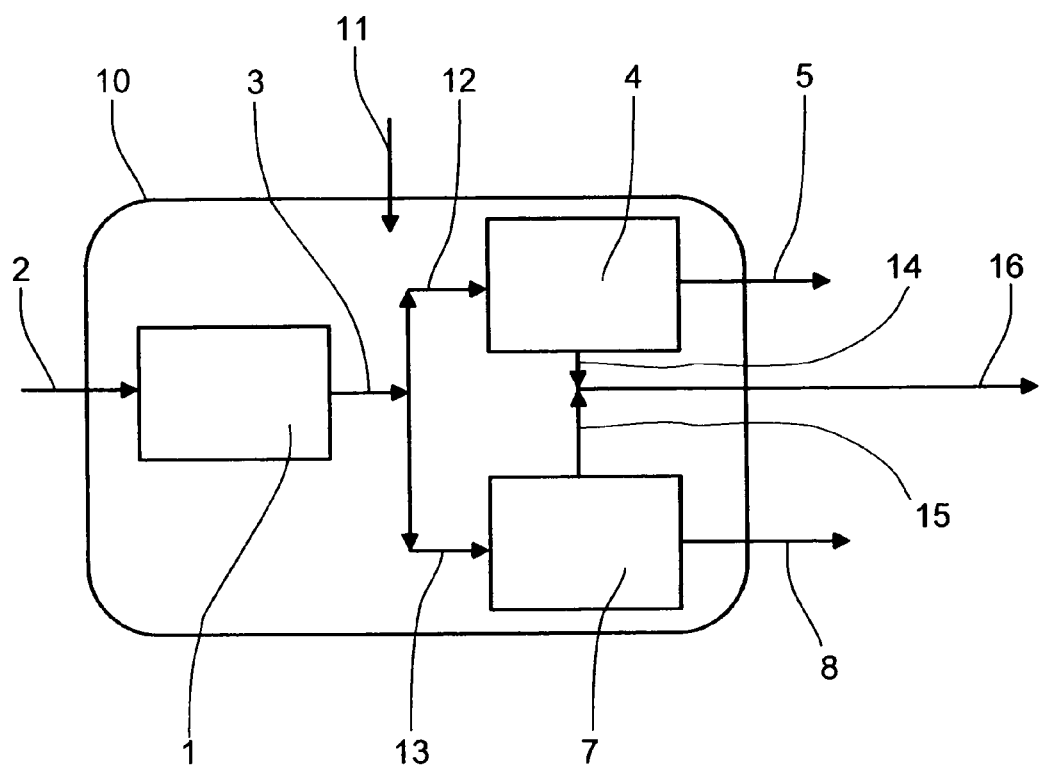
FIG. 2 shows a process flow diagram of the process according to the invention in which the water content and the methane content are measured in parallel.

FIG. 2 shows a process flow diagram of the process according to the invention in which the water content and the methane content are determined in two cavity ring-down spectrometers connected in parallel. To this end, as in the embodiment shown in FIG. 1, an ammonia stream 2 comprising traces of oxygen- and/or carbon-comprising compounds is first fed to the cracker 1. In the cracker, the ammonia is split into hydrogen and nitrogen. Owing to the high hydrogen excess, the oxygen- and/or carbon-comprising compounds are converted to water and methane respectively. The gas stream 3 which comprises hydrogen, nitrogen, water, methane and traces of ammonia and is formed here is divided into a first substream 12 which is fed to the first cavity ring-down spectrometer 4, and a second substream 13 which is fed to the second cavity ring-down spectrometer 7. To measure the water content, a substream 5 is separated from the first substream 12 in the first cavity ring-down spectrometer 4 and the water content is determined therein. The remaining gas as the first offgas stream 14 is mixed with a second offgas stream 15 and either released to the environment as offgas 16 which comprises hydrogen, nitrogen, small amounts of water and methane and ammonia, or fed again to the ammonia synthesis. The first offgas stream 14 and the second offgas stream 15 may also each be released separately to the environment or fed to the ammonia synthesis. Mixing to give the offgas stream 16, as shown in FIG. 2, is not required.

The second offgas stream 15 is the gas stream which is not required to determine the carbon content in the second cavity ring-down spectrometer 7. The carbon content is determined in the substream 8 which is separated from the second substream 13. After the determination of the carbon content, the substream 8 is released to the environment.

In the embodiment shown in FIG. 2 too, the cracker, the first cavity ring-down spectrometer 4, the second cavity ring-down spectrometer 7 and all lines connecting the cracker 1 and the cavity ring-down spectrometers 4 and 7 are enclosed by a casing 10 which is flooded with an inert gas. In this embodiment too, inert gas escaping from the casing 10 can be replaced by means of an inert gas feed 11.

REFERENCE NUMERAL LIST

1 Cracker
2 Ammonia stream
3 Gas stream
4 First cavity ring-down spectrometer
5 Substream
6 Gas stream
7 Second cavity ring-down spectrometer
8 Substream
9 Gas stream
10 Casing
11 Inert gas feed
12 First substream
13 Second substream
14 First offgas stream
15 Second offgas stream
16 Offgas

What is claimed is:

1. A process for determining the total oxygen content and the total carbon content of ammonia which is intended to be designated as high-purity comprising the steps:
    a) splitting the ammonia into a gas comprising nitrogen and hydrogen, then
    b) essentially fully reacting oxygen of all oxygen-containing compounds present to give water and carbon of all carbon containing-compounds present in the gas with hydrogen to give methane, then
    c) determining the water content and the methane content in the gas, then
    d) determining the total oxygen content from the water content and the total carbon content from the methane content.

2. The process according to claim 1, wherein the water content and the methane content are each determined by cavity ring-down spectroscopy.

3. The process according to claim 1, wherein the ammonia is split and the oxygen- and/or carbon-containing compounds are converted to water and/or methane at a temperature of at least 600° C.

4. The process according to claim 1, wherein the splitting-of ammonia and of the oxygen- and/or carbon-containing compounds proceeds virtually simultaneously with the conversion of hydrogen and oxygen to water.

5. The process according to claim 1, wherein the water content and the methane content are detected separately.

6. The process according to claim 5, wherein the water content and the methane content are detected by measuring devices connected in series.

7. The process according to claim 5, wherein the water content and the methane content are detected by measuring devices connected in parallel.

8. The process according to claim 1, wherein the device for splitting the ammonia and the oxygen- and carbon-containing compounds, the devices for detecting the oxygen content and the carbon content, and all connections between these devices are operated under an inert gas atmosphere and/or in an evacuated protective system.

9. The process according to claim 8, wherein the inert gas is essentially free of oxygen- and carbon-containing compounds.

10. The process according to claim 8, wherein the inert gas is a noble gas, nitrogen, hydrogen or the gas mixture formed by the splitting of ammonia.

11. The process according to claim 1, wherein the oxygen and/or carbon-containing compounds comprise carbon monoxide, carbon dioxide, hydrocarbons, oxygen and water.

12. An apparatus for performing the process according to claim 1, comprising a cracker for splitting the ammonia and at least one cavity ring-down spectrometer for detecting the water content and/or carbon content, the cracker and the at least one spectrometer, and also all devices and connecting lines between the cracker and the spectrometer, being surrounded by an inert gas.

13. The apparatus according to claim 12, wherein a reactor in which the carbon of the carbon-containing compounds reacts with hydrogen to give methane and the oxygen of the oxygen-containing compounds reacts with hydrogen to give water is connected downstream of the cracker.

14. The apparatus according to claim 12, wherein the reaction of hydrogen with the oxygen of the oxygen-containing compounds to give water and the reaction of hydrogen with the carbon of the carbon-containing compounds to give methane proceeds in the cracker.

15. The process according the claim 1, wherein the ammonia comprises at least one compound selected from the group consisting of oxygen containing compounds and carbon containing compounds.

* * * * *